US012390228B2

(12) United States Patent
Tsuji et al.

(10) Patent No.: US 12,390,228 B2
(45) Date of Patent: Aug. 19, 2025

(54) CUTTING MACHINING APPARATUS

(71) Applicant: NISSIN MANUFACTURING CO., LTD., Kyoto (JP)

(72) Inventors: Hidekazu Tsuji, Kyoto (JP); Chiori Mochizuki, Kyoto (JP); Kenji Inoue, Kyoto (JP); Koji Tanaka, Kyoto (JP)

(73) Assignee: NISSIN MANUFACTURING CO., LTD., Kyoto (JP)

( * ) Notice: Subject to any disclaimer, the term of this patent is extended or adjusted under 35 U.S.C. 154(b) by 270 days.

(21) Appl. No.: 18/335,389

(22) Filed: Jun. 15, 2023

(65) Prior Publication Data
US 2024/0115272 A1   Apr. 11, 2024

(30) Foreign Application Priority Data
Jun. 15, 2022   (JP) .................................. 2022-096853

(51) Int. Cl.
*A61B 17/16* (2006.01)
*B26D 7/22* (2006.01)
*B26D 7/26* (2006.01)

(52) U.S. Cl.
CPC ................ *A61B 17/16* (2013.01); *B26D 7/22* (2013.01); *B26D 7/26* (2013.01); *A61B 2017/1602* (2013.01)

(58) Field of Classification Search
CPC .......... A61B 174/16; A61B 2017/1602; B26D 7/22; B26D 7/26
See application file for complete search history.

(56) References Cited

U.S. PATENT DOCUMENTS

| | | | |
|---|---|---|---|
| 11,766,753 B2 * | 9/2023 | Li | B23Q 11/1076 409/228 |
| 11,864,729 B2 * | 1/2024 | Shelton, IV | A61B 1/000094 |
| 12,002,571 B2 * | 6/2024 | Shelton, IV | A61B 18/1445 |
| 12,207,881 B2 * | 1/2025 | Shelton, IV | G16H 20/40 |
| 12,257,013 B2 * | 3/2025 | Scheib | G01S 17/86 |
| 2015/0183130 A1 * | 7/2015 | Gadd | B24B 55/02 83/100 |
| 2017/0333053 A1 * | 11/2017 | Li | A61B 17/16 |
| 2019/0175272 A1 * | 6/2019 | Khan | A61B 34/35 |
| 2019/0343112 A1 * | 11/2019 | Woods | A61B 17/16 |
| 2023/0165594 A1 * | 6/2023 | Harris | G05B 19/182 606/180 |
| 2024/0108364 A1 * | 4/2024 | Penner | A61B 17/1775 |

FOREIGN PATENT DOCUMENTS

JP   S62074943 U   5/1987

* cited by examiner

*Primary Examiner* — Omar Flores Sanchez
(74) *Attorney, Agent, or Firm* — Ohlandt, Greeley and Perle, L.L.P.

(57) ABSTRACT

A cutting machining apparatus includes: a holding unit including a workpiece holder, a tool holder, and a unit body; a head positioned facing the holding unit and including a chuck holding a tool; an interior case of a box shape including, in a peripheral wall, a first opening through which the holding unit is inserted and a second opening through which the head is inserted and housing the workpiece holder, the tool holder, and the chuck disposed inside; a first cover occluding between the head and the outer periphery of the first opening of the interior case, a second cover occluding between the holding unit and the outer periphery of the second opening of the interior case, and a cooling source cooling the tool holder from within the unit body via a heat transfer member.

20 Claims, 12 Drawing Sheets

CUTTING MACHINING APPARATUS

FIELD OF THE INVENTION

The present disclosure relates to a cutting machining apparatus.

BACKGROUND OF THE INVENTION

To greatly reduce the burden on a patient by eliminating the need for reoperation to remove a thread after a fractured bone has been fused, threads are being made for joining bones with each other by cutting machining a bone fragment obtained by cutting out a bone of a patient themselves, and these threads are used to join a fractured bone of the patient. In such a case, the burden on the patient is required to be reduced by minimizing the size of the bone fragment cut out from the patient's bone for making the thread. In addition, a machining center capable of stably performing high-precision machining of workpieces has been proposed (refer to, for example, Utility Model Application Publication No. S62-74943).

Incidentally, when machining a bone fragment using, for example, a machining center as described in Utility Model Application Publication No. S62-74943, there is a risk that excessive heat generated due to friction between the tool and the bone fragment may be applied to the bone fragment. Further, it has been reported that when excessive heat is applied to a bone fragment, activation of the bone fragment is inhibited, reducing the rate of fusion of the thread after joining a fractured part using the thread made from the bone fragment. Therefore, a cutting machining apparatus capable of suppressing the temperature rise of a bone fragment when machining the bone fragment is required. In addition, when a thread is made by cutting machining, foreign matters present in an area where the thread is made need to be minimized from a viewpoint of preventing infection of the patient caused by bacteria attached to the produced thread. However, in the machining center described in Utility Model Application Publication No. S62-74943, since the machining area is exposed to outside air, there is a risk that the thread is contaminated by foreign matters present around the bone fragment to be machined.

The present disclosure is made in consideration of the above problems. Thus, an objective of the present disclosure is to provide a cutting machine apparatus capable of suppressing the temperature rise of a workpiece during machining while increasing the cleanliness of an area where cutting machining is conducted.

SUMMARY OF THE INVENTION

In order to achieve the above objective, the cutting machining apparatus according to the present disclosure includes:
- a holding unit including a workpiece holder that holds a workpiece, a tool holder having a bottomed cylindrical shape and holding a tool in a state in which the tool is inserted inside, and a unit body that secures the tool holder in such a way that, in a state in which the tool is not inserted into the tool holder, the inside of the tool holder is in communication with the outside and the outer wall of the tool holder is isolated from the outside;
- a head positioned facing the holding unit and including a chuck holding the tool held by the tool holder;
- an interior case including, in a peripheral wall, a first opening through which the holding unit is inserted and a second opening through which the head is inserted and housing the workpiece holder, the tool holder, and the chuck disposed inside;
- a first cover formed of a soft material and occluding between the holding unit and an outer periphery of the first opening in the interior case;
- a second cover formed of a soft material and occluding between the head and an outer periphery of the second opening in the interior case; and
- a cooling mechanism cooling the tool holder from within the unit body.

According to the present disclosure, at least the workpiece holder, the tool holder, and the chuck of the holding unit are disposed inside the interior case. The first cover occludes between the holding unit and the outer periphery of the first opening in the interior case, and the second cover occludes between the head and the outer periphery of the second opening in the interior case. The tool holder is secured to the unit body in such a way that, in a state in which the tool is not inserted therein, the inside of the tool holder is in communication with the outside of the unit body and the outer wall of the tool holder is isolated from the outside of the unit body. This makes it possible to form an area for cutting machining, inside the interior case, that is isolated from the outside of the interior case, thereby suppressing foreign matters present outside of the interior case from entering into the area where cutting machining is conducted. Furthermore, the cooling mechanism cools the tool holder that holds the tool from within the unit body, thereby suppressing the temperature rise of a workpiece during machining while increasing the cleanliness of the area where the cutting machining is conducted.

BRIEF DESCRIPTION OF DRAWINGS

A more complete understanding of this application can be obtained when the following detailed description is considered in conjunction with the following drawings, in which.

DETAILED DESCRIPTION OF THE INVENTION

Embodiment 1

A cutting machining apparatus according to an embodiment of the present disclosure is described below with reference to the drawings. The cutting machining apparatus according to the present embodiment includes: a holding unit including a workpiece holder that holds a workpiece; a tool holder holding a tool; and a box-shaped unit body; a head positioned facing the holding unit and including a chuck that holds a tool held by the tool holder; an interior case of a box shape including, in a peripheral wall, a first opening through which the head is inserted and a second opening through which the holding unit is inserted and housing the workpiece holder, the tool holder, and the chuck disposed inside; a first cover formed of a soft material and occluding between the head and the outer periphery of the first opening in the interior case; a second cover formed of a soft material and occluding between the holding unit and the outer periphery of the second opening in the interior case; and a cooling mechanism for cooling the tool holder from within the unit body. Here, the tool holder has a bottomed cylindrical shape and holds the tool in a state in which the tool is inserted inside. The unit body is box-shaped, and, secures the tool holder in such a way that, in a state in which the tool is not inserted into the tool holder, the inside of the tool holder is in communication with the outside of the tool holder and the outer wall of the tool holder is isolated from the outside.

Figure 1:
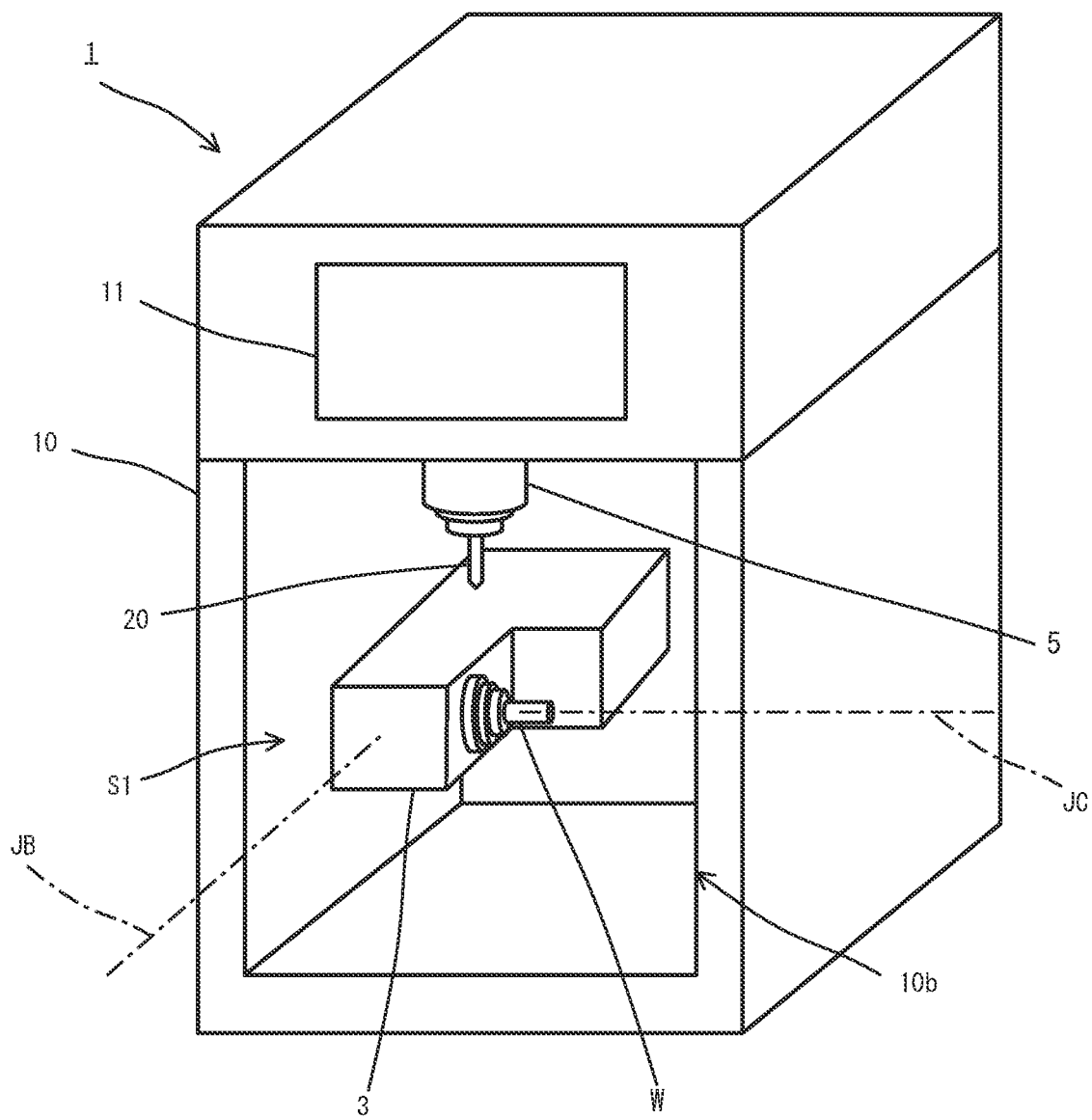
FIG. 1 is a schematic diagram of a cutting machining apparatus according to Embodiment 1 of the present disclosure.
Figure 1:
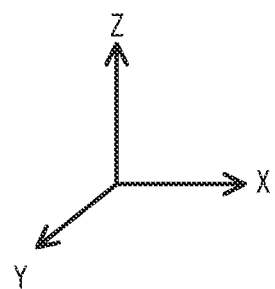
Figure 2:
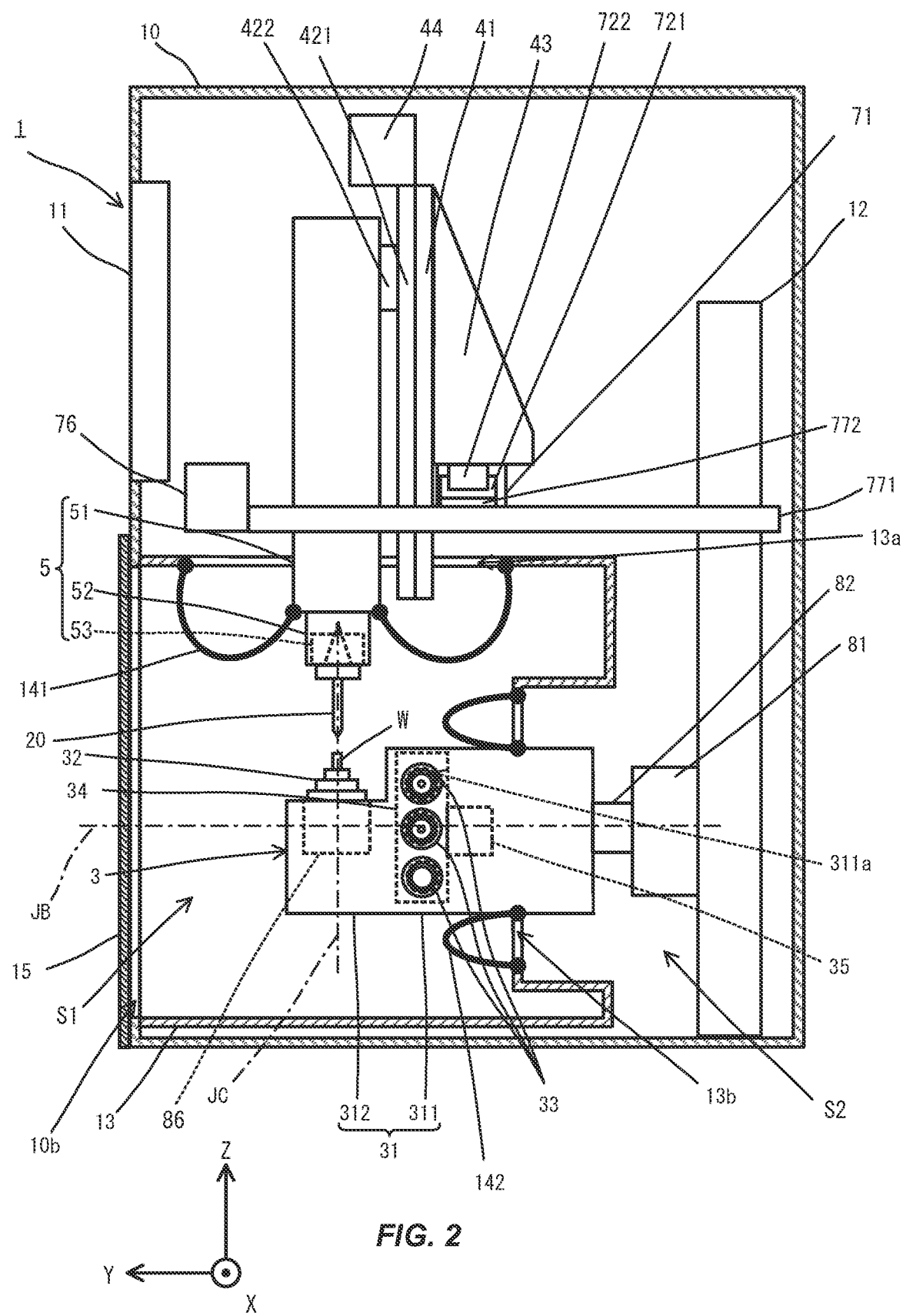
FIG. 2 is a partially broken side view of the cutting machining apparatus according to Embodiment 1.

As illustrated in FIG. 1, a cutting machining apparatus 1 according to the present embodiment includes a holding unit 3 that holds a workpiece W, a head 5 that is positioned facing the holding unit 3 and holds a tool 20, a controller (not illustrated) that controls the operation of the holding unit 3 and the head 5, and a display panel 11. In addition, the cutting machining apparatus 1 includes a chassis 10 of a rectangular box shape that has an opening 10*b* in the +Y direction-side side wall formed for inserting and removing a workpiece W and housing the holding unit 3, the head 5, and the controller disposed inside. Although not illustrated in FIG. 1, the opening 10*b* can be occluded by a door 15 described later. Furthermore, as illustrated in FIG. 2, the cutting machining apparatus 1 includes: an interior case 13 of a rectangular box shape one side of which is open and in which portions of the holding unit 3 and the head 5 are disposed; a first cover 141 and a second cover 142 formed of a soft material; and a door 15 covering the opening 10*b* from the +Y direction side. The cutting machining apparatus 1 also includes a lift drive 44 that raises and lowers the head 5 in a vertical direction, an X-direction drive 71 that drives the head 5 along the X-axis direction, and a Y-direction drive 76 that drives the head 5 along the Y-axis direction. The chassis 10 has the interior case 13 disposed inside and the display panel 11 mounted on the +Z direction side of the opening 10*b* in the +Y direction-side side wall. The display panel 11 displays, for example, a progress status of the cutting machining processing performed on the workpiece W.

The interior case 13 has a machining area S1 formed inside where machining of the workpiece W is conducted. The machining area S1 is enclosed by the interior case 13 and the door 15. The interior case 13 is disposed inside the chassis 10 in a posture in which the open portion is oriented toward the opening 10*b* side of the chassis 10 and has openings 13*a* and 13*b* provided in the +Z direction side peripheral wall and the −Y direction side peripheral wall, respectively. Here, the opening 13*a* is a first opening through which the head 5 is inserted, and the opening 13*b* is a second opening through which the holding unit 3 is inserted. In addition, a support member 12 that supports the head 5, the holding unit 3, and the like is disposed in an area S2 outside the interior case 13 within the chassis 10.

The head 5 includes a long rotary spindle 52 provided with a chuck 53, at one end of the longitudinal direction, that holds the tool 20 and a spindle drive 51 that rotates the rotary spindle 52 about a central axis along the longitudinal direction thereof. The chuck 53 includes a chuck (not illustrated) and an actuator (not illustrated) that drives the chuck, and the chuck opens and closes according to a control signal input from the controller. The head 5 is secured to a slider 422 that is slidably held on a rail 421 extending along the Z axis direction on the +Y direction side of the base 41. The lift drive 44 includes: a long feed screw (not illustrated) arranged along the Z-axis direction and screwed to a nut (not illustrated) provided on a portion of the slider 422; and a motor (not illustrated) coupled to the feed screw to rotate the feed screw. The lift drive 44 then raises and lowers the slider 422 and the head 5 secured to the slider 422 along the Z-axis direction by rotating the feed screw arranged along the Z-axis direction.

The base 41 is also secured via a bracket 43 to a slider 722 that is slidably held on a rail 721 extending along the X-axis direction. The X-direction drive 71 includes: a long feed screw (not illustrated) arranged along the X-axis direction and screwed to a nut (not illustrated) provided on a portion of the bracket 43; and a motor (not illustrated) coupled to the feed screw to rotate the feed screw. The X-direction drive 71 then moves the slider 722 and the base 41 secured to the slider 722 along the X-axis direction by rotating the feed screw arranged along the X-axis direction. As a result, the X-direction drive 71 moves the base 41 and the head 5 together along the X-axis direction via the feed screw. The rail 721 is supported by sliders 772 that are slidably held on two rails 771 of which longitudinal ends extend along the Y-axis direction. The Y-direction drive 76 includes: a long feed screw (not illustrated) arranged along the Y-axis direction and screwed to a nut (not illustrated) provided on a portion of the base 41; and a motor (not illustrated) coupled to the feed screw to rotate the feed screw. The Y-direction drive 76 then moves the sliders 772 and the rail 721 supported by the sliders 772 along the Y-axis direction by rotating the feed screw arranged along the Y-axis direction. As a result, the Y-direction drive 76 moves the rail 721, the slider 722, the base 41, and the head 5 together via the feed screw along the Y-axis direction.

Figure 3:
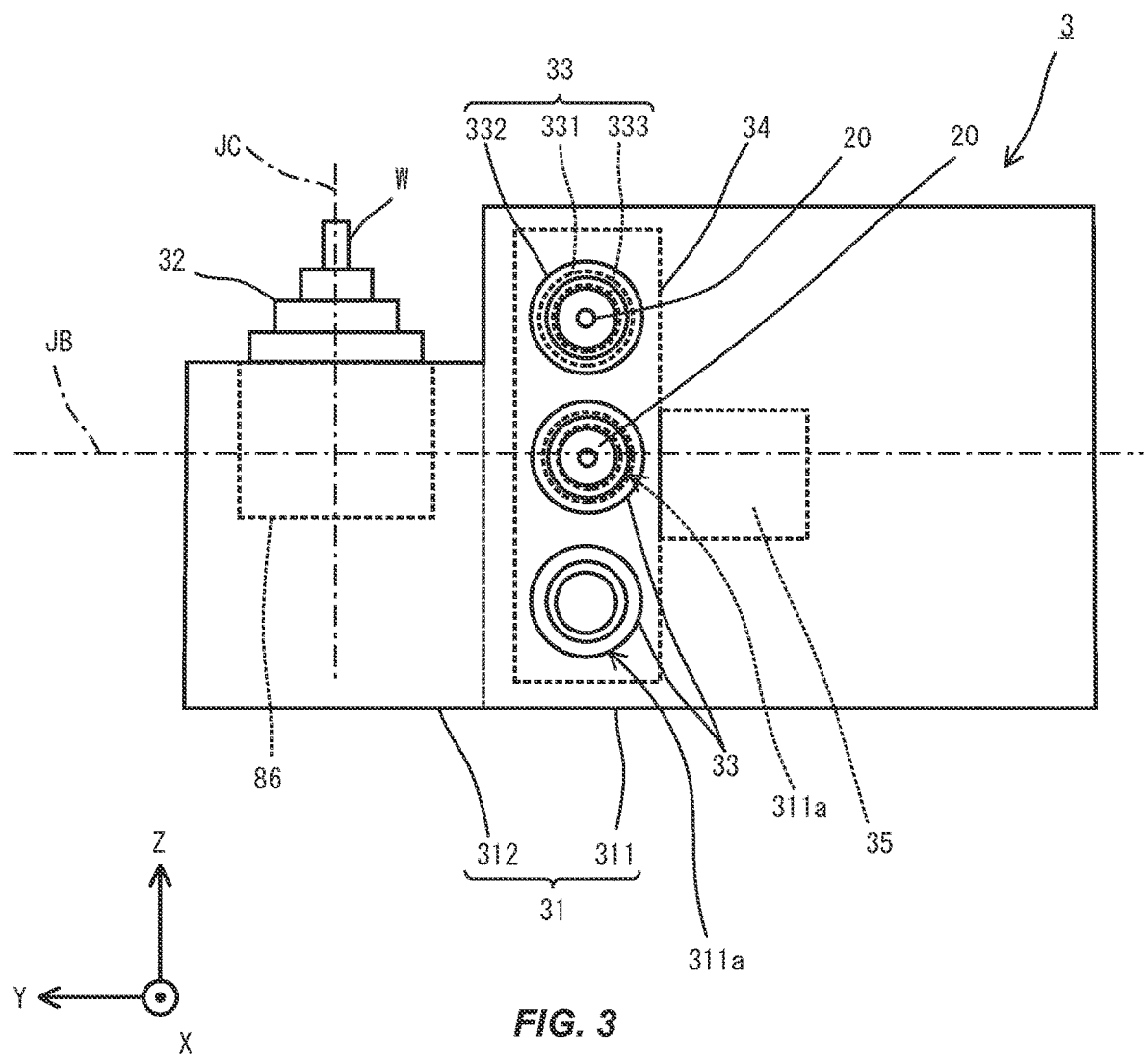
FIG. 3 is a side view of a holding unit according to Embodiment 1.

As illustrated in FIG. 3, the holding unit 3 includes: a workpiece holder 32 that holds a workpiece W; a tool holder 33 that has a substantially bottomed circular shape and holds the tool 20 in a state in which the tool 20 is inserted inside; a box-shaped unit body 31; a heat transfer member 34; and a cooling source 35. As illustrated in FIG. 2, the holding unit 3 includes: a rotary drive 81 that causes the entire unit body 31 to rotate about a rotational axis (hereinafter, referred to as "B axis") JB extending along the longitudinal direction of the unit body 31; and a rotary drive 86 that causes the workpiece holder 32 to rotate about a rotational axis extending along a direction orthogonal to the longitudinal direction of the unit body 31 (hereinafter, referred to as the "C axis") JC.

The rotary drive 86 includes a motor that is disposed inside the unit body 31 and rotates a shaft (not illustrated) that extends along the C axis and of which tip is coupled to the workpiece holder 32. The rotary drive 81 includes a motor that supports the −Y direction-side end of a shaft 82 having a cylindrical shape and extending along the B axis to rotate the shaft 82 about the B axis. The unit body 31 is secured to the +Y direction-side end of the shaft 82. The rotary drive 81 is supported by the support member 12 provided on the outside of the interior case 13 within the chassis 10.

The unit body 31 includes a hollow rectangular first section 311 and a rectangular box-shaped second section 312 that is continuous to the first section 311 at the +Y direction-side end of the first section 311, as illustrated in FIG. 3. The first section 311 is secured to the shaft 82 at the −Y direction side end of the first section 311, as illustrated in FIG. 2. Then, when the shaft 82 of the rotary drive 81 rotates about the B axis, the unit body 31 rotates about the B axis accordingly. The first section 311 has three openings 311*a* formed in the side wall along the Z-axis direction. The workpiece holder 32 is a chuck that grips the proximal end of a long workpiece W. The workpiece holder 32 is secured to the peripheral wall of the second section 312 of the unit body 31.

Figure 4A:
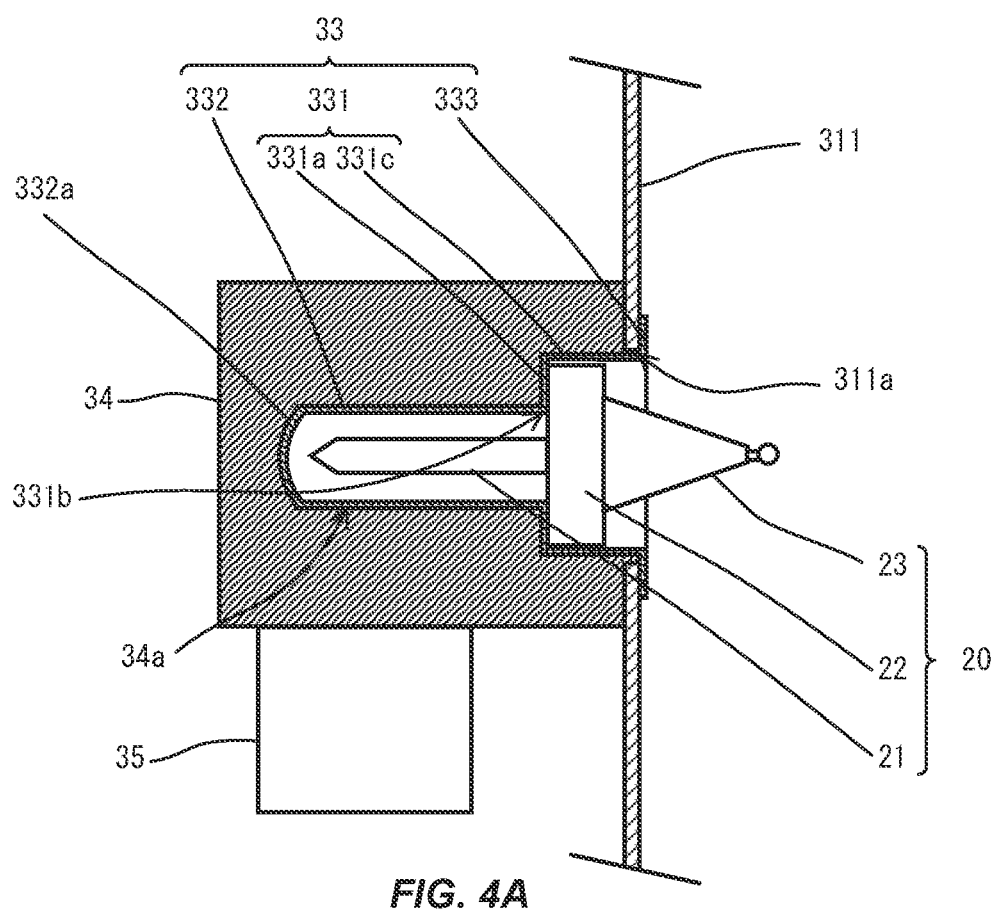
FIG. 4A is a cross-sectional view of a tool holder and a heat transfer member according to Embodiment 1.
Figure 4B:
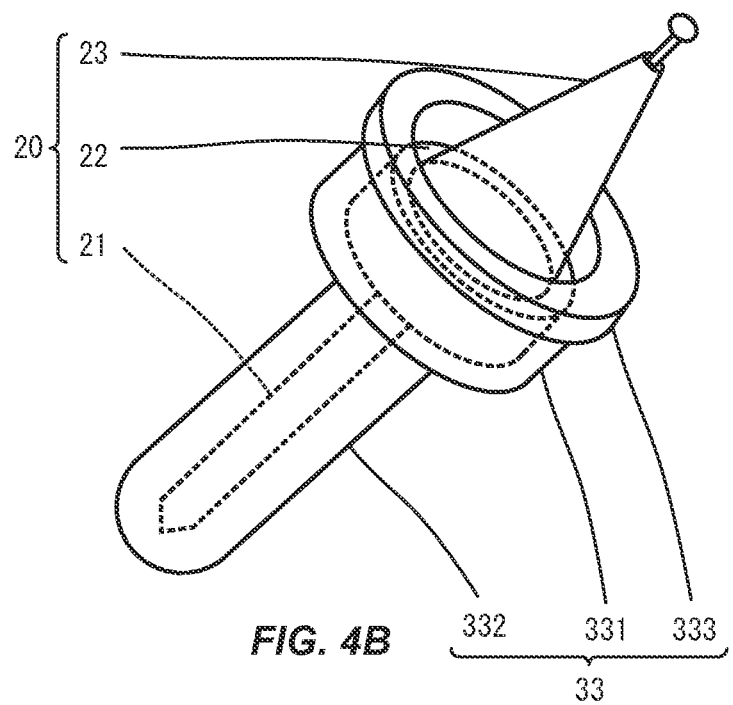
FIG. 4B is a perspective view of the tool holder according to Embodiment 1.

The tool holder 33 is secured to the unit body 31 in such a way that, in a state in which the tool 20 is not inserted in the tool holder 33, the inside of the tool holder 33 is in communication with the outside of the unit body 31 and the outer wall of the tool holder 33 is isolated from the outside of the unit body 31. Here, as illustrated in FIGS. 4A and 4B, the tool 20 includes: a disc-shaped tool body 22; a blade 21, for cutting a workpiece, formed continuously with the tool body 22 and protruding from one side in the thickness direction of the tool body 22; and a shank 23 formed continuously with the tool body 22 and protruding from the other side in the thickness direction of the tool body 22 and held by the chuck 53 of the head 5. The tool holder 33 includes: a tool body housing 331 formed of metal such as aluminum, copper, or the like, and housing the tool body 22 of the tool 20 disposed inside; a blade housing 332 housing the blade 21 of the tool 20 disposed inside; and an outer flange 333. Here, the tool body housing 331 has a bottomed cylindrical shape and has a bottom wall 331*a* as a first bottom, through which a through hole 331*b* penetrates in a thickness direction of the bottom wall 331*a*, and the tool body 22 of the tool 20 is disposed inside the tool body housing 331 in a state in which the tool body 22 abuts at least one of the bottom wall 331*a* and the side wall 331*c*. The blade housing 332 has a bottomed cylindrical shape of which inner diameter smaller than the inner diameter of the tool body housing 331. The blade housing 332 has a bottom wall 332*a* as a second bottom wall, and the entire end opposite the bottom wall 332*a* is formed continuously with the outer periphery of the through hole 331*b* in the bottom wall 331*a*. The outer flange 333 extends from the end of the tool body housing 331, opposite the bottom wall 331*a*, in a direction orthogonal to the cylindrical axis of the tool body housing 331 and away from the cylindrical axis of the tool body housing 331. The tool holder 33 is secured by securing the outer flange 333 to the peripheral wall of the unit body 31 in a state in which the outer flange 333 is exposed outside the unit body 31 through the opening 311*a* provided in the peripheral wall of the unit body 31. Here, between the outer flange 333 and the outer periphery of the opening 311*a* of the unit body 31 may be sealed by a sealing member (not illustrated).

The heat transfer member 34 is formed of metal such as aluminum, copper, or the like, in a rectangular shape and is arranged to cover the tool body housing 331 and blade housing 332 of the tool holder 33. In addition, the heat transfer member 34 has recesses 34*a* that open to portions corresponding to the three openings 311*a* of the unit body 31 and into which the tool holders 33 are inserted. The tool holder 33 is inserted inside the recess 34*a* of the heat transfer member 34, and the outer flange 333 is secured to the heat transfer member 34 in a state in which the outer flange 333 is in close contact with the outer periphery of the recess 34*a* in the heat transfer member 34. The cooling source 35 includes a Peltier element, for example, and is arranged in a state in which the cooling source 35 is in contact with the heat transfer member 34 inside the unit body 31 to maintain the heat transfer member 34 at a preset temperature. The heat transfer member 34 and the cooling source 35 form a cooling mechanism for cooling the tool holder 33 from within the unit body 31. The tool holder 33 then holds the tool 20 in a state in which the shank 23 is exposed outside the holding unit 3 within the interior case 13, as illustrated in FIG. 2.

The first cover 141 is formed of a soft material such as a thin rubber film, a vinyl film, or the like, and is preferably sterilized using, for example, ethylene oxide gas. The first cover 141 is cylindrical having a shape in which one end in the cylindrical axial direction is reduced in diameter toward the other end, the entire one end in the cylindrical axial direction is secured to the outer periphery of the opening 13*a* of the interior case 13, and the other entire end in the cylindrical axial direction is secured to the spindle drive 51 of the head 5. The second cover 142 is also formed of a soft material such as a thin rubber film, a vinyl film, or the like, and is preferably sterilized using, for example, ethylene oxide gas. The second cover 142 is cylindrical having a shape in which one end in the cylindrical axial direction is reduced in diameter toward the other end, and the entire one end in the cylindrical axial direction is secured to the outer periphery of the opening 13*b* of the interior case 13 and the entire other end in the cylindrical axial direction is secured to the unit body 31 of the holding unit 3.

The controller includes: for example, a programmable logic controller (PLC) including a central processing unit (CPU) unit and an input/output control unit; and an input device, such as a keyboard and a touch panel, connected to the PLC. The controller outputs control signals to driving circuits for driving the spindle drive 51, the lifting drive 44, the X-direction drive 71, the Y-direction drive 76, the rotary drives 81, 86, and the chuck 53, respectively to control the operations thereof.

Figure 5A:
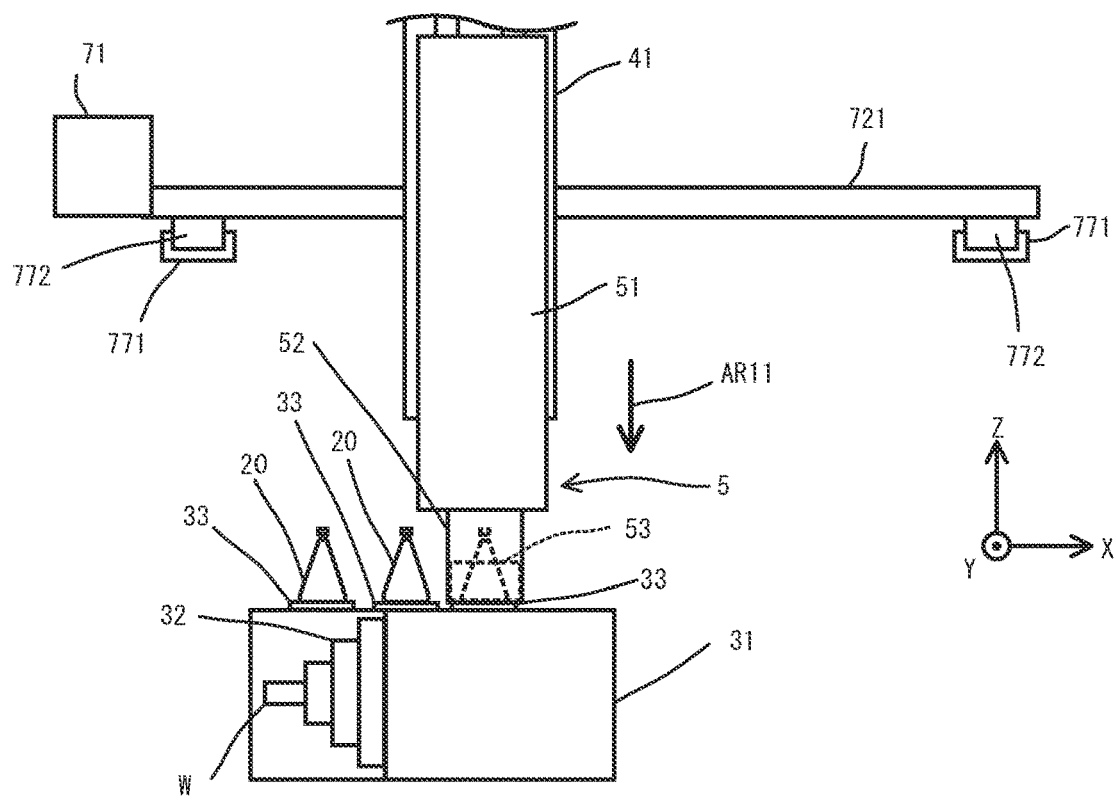
FIG. 5A is a front view illustrating a head of the cutting machining apparatus descending to hold a tool according to Embodiment 1.
Figure 5B:
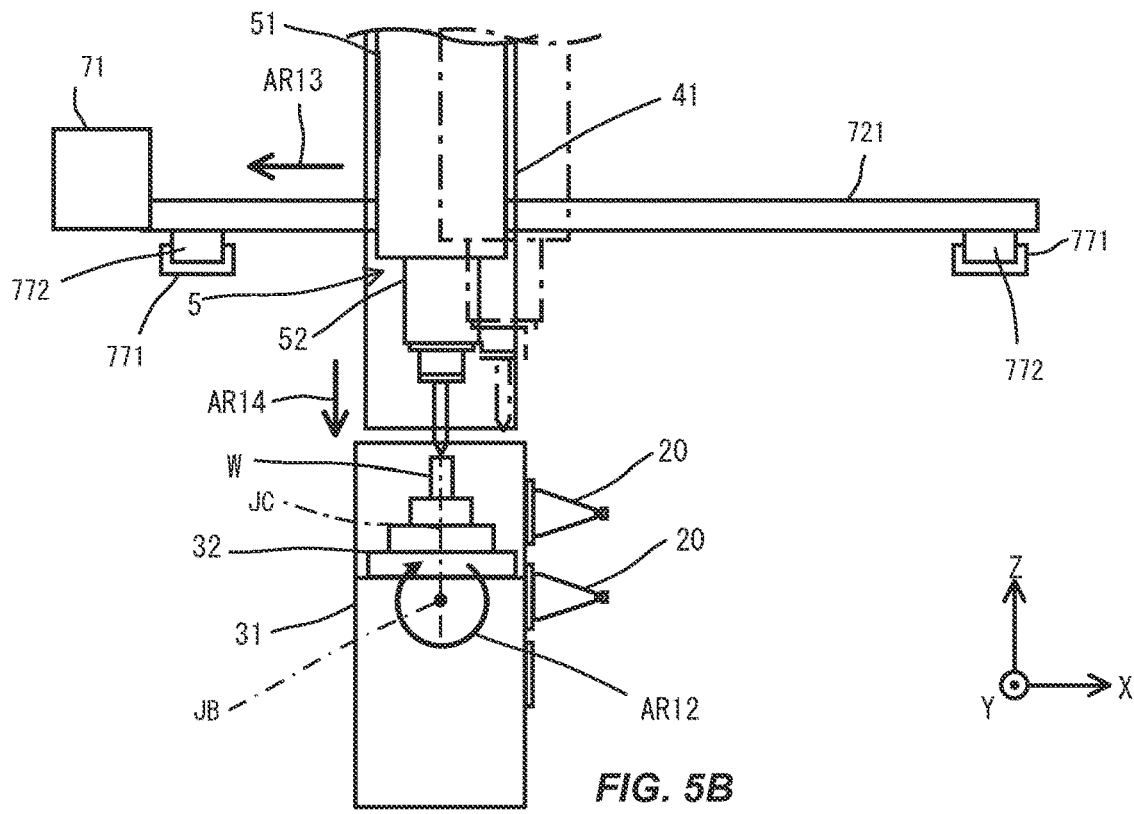
FIG. 5B is a front view illustrating the cutting machining apparatus machining a workpiece according to Embodiment 1.

Next, an operation of the cutting machining apparatus 1 according to the present embodiment is described with reference to FIGS. 5A and 5B. Here, an example of machining performed by drilling a workpiece W by a drill, which is the tool 20, along the longitudinal direction of the long workpiece W is described. It is assumed that tools 20 to be used are held in the three tool holders 33 of the holding unit 3, and the workpiece W is held in the workpiece holder 32. Furthermore, it is assumed that the holding unit 3 is maintained in a posture in which the tool holder 33 is oriented toward the +Z direction. First, as illustrated in FIG. 5A, in a state in which the head 5 is positioned on the +Z direction side of the tool holder 33 of the holding unit 3, the cutting machining apparatus 1 lowers the head 5 in the −Z direction as indicated by the arrow AR 11, causing the head 5 to hold one of the tools 20. The cutting machining apparatus 1 then raises the head 5 holding the tool 20 in the +Z direction. Subsequently, by rotating the holding unit 3 about the B axis JB as indicated by the arrow AR12 in FIG. 5B, the cutting machining apparatus 1 sets the workpiece holder 32 holding the workpiece W in a posture oriented toward the +Z direction. The cutting machining apparatus 1 then moves the head 5 in the X-axis direction and the Y-axis direction in such a way that the position of the tool 20 is in alignment with the workpiece W in the Z-axis direction, as indicated by the arrow AR13. Next, the cutting machining apparatus 1 performs cutting machining of the workpiece W by lowering the head 5 in the −Z direction and causing the tip of the tool 20 to contact the workpiece W, as indicated by the arrow AR 14, while rotating the rotary spindle 52 without moving the workpiece holder 32.

Note that, when machining is conducted by drilling into the side wall along the longitudinal direction of the workpiece W, the cutting machining apparatus 1 maintains the holding unit 3 in a posture in which the workpiece holder 32 is oriented toward the ±X direction. Subsequently, the cutting machining apparatus 1 performs cutting machining on the workpiece W with the tool 20 by lowering the head 5 in the −Z direction and causing the tip of the tool 20 to contact the workpiece W, while rotating the rotary spindle 52 without moving the workpiece holder 32. When the tool 20 is a threading tap, the cutting machining apparatus 1 can also thread the workpiece W at a high speed by lowering the head 5 in the −Z direction and causing the tip of the tool 20 to contact the workpiece W, while rotating the rotary spindle 52, as well as, rotating the workpiece holder 32 in a direction opposite to the rotating direction of the rotary spindle 52.

As described above, according to the cutting machining apparatus 1 according to the present embodiment, the workpiece holder 32, the tool holder 33, and the chuck 53 are disposed inside the interior case 13, the first cover 141 occludes between the head 5 and the outer periphery of the opening 13a in the interior case 13, and the second cover 142 occludes between the holding unit 3 and the outer periphery of the opening 13b in the interior case 13. The tool holder 33 is secured to the unit body 31 in such a way that, in a state in which the tool 20 is not inserted in the tool holder 33, the inside of the tool holder 33 is in communication with the outside of the unit body 31 of the holding unit 3 and the outer wall of the tool holder 33 is isolated from the outside of the unit body 31. As a result, the machining area S1 where cutting machining is conducted and that is isolated from the outside of the interior case 13 can be formed inside the interior case 13, thereby suppressing foreign matters present outside the interior case 13 from entering into the machining area S1. In addition, since the heat transfer member 34 and the cooling source 35 cool the tool holder 33 that holds the tool 20 from within the unit body 31, the temperature rise of the workpiece W during machining of the workpiece W is suppressed while increasing the cleanliness of the machining area S1.

Incidentally, cooling of a tool 20 by air blow or coolant is often carried out to suppress an excessive temperature rise of the tool 20 and a workpiece W during cutting machining. However, when the workpiece W is a bone fragment, as in the cutting machining apparatus 1 according to the present embodiment, there is a concern that the workpiece W becomes excessively dry with an air-blow cooling method. In addition, with a cooling method using coolant, contamination of the workpiece W is a concern. To counter such concerns, with the cutting machining apparatus 1 according to the present embodiment, the tool 20 can be cooled while the tool 20 is disposed in the clean machining area S1, and thus drying or contamination of the workpiece W can be suppressed.

In addition, the tool 20 according to the present embodiment is formed by continuously integrating the tool body 22, the blade 21, and the shank 23. As a result, the frictional heat generated at the blade 21 during machining of the workpiece W by the tool 20 is efficiently transmitted to the tool body 22 and the shank 23, and thus the frictional heat generated at the blade 21 can be efficiently dissipated to the head 5 via the tool body 22 and the shank 23. Thus, an excessive temperature rise of the tool 20 and the workpiece W during cutting machining can be suppressed.

Embodiment 2

The cutting machining apparatus according to the present embodiment differs from Embodiment 1 in that the present embodiment includes a first holding unit that holds a workpiece and a second holding unit that is separate from the first holding unit and holds a tool. The second holding unit according to the present embodiment includes: a tool holder of a bottomed cylindrical shape; and a unit body that has a box shape and secures the tool holder in a state in which the outer wall of the tool holder is isolated from the outside, in which the inside of the tool holder is in communication with the outside in a state in which a tool is not inserted in the tool holder. In addition, the inside of the unit body is filled with refrigerant in such a manner the refrigerant contacts at least a portion of the tool holder.

Figure 6:
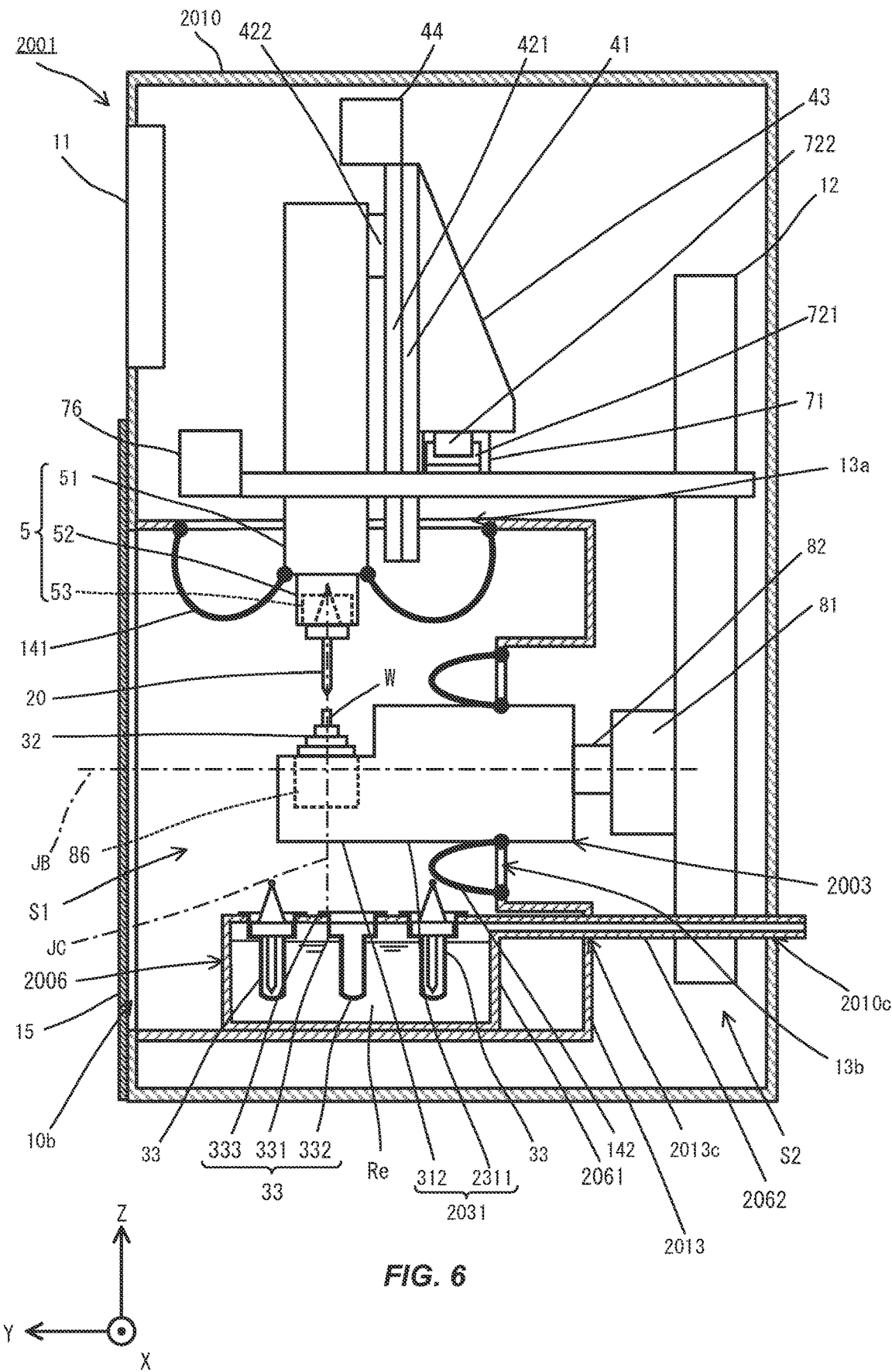
FIG. 6 is a partially broken side view of a cutting machining apparatus according to Embodiment 2 of the present disclosure.

As illustrated in FIG. 6, a cutting machining apparatus 2001 according to the present embodiment includes a head 5, a holding unit 2003 that holds a workpiece W, a holding unit 2006 that holds a tool 20, a controller (not illustrated), a chassis 2010, an interior case 2013, a first cover 141, a second cover 142, and a door 15. Note that, in FIG. 6, the same components as those in Embodiment 1 are denoted by the same numeral signs as those in FIG. 2. The cutting machining apparatus 2001 also includes a lift drive 44, an X-direction drive 71, and a Y-direction drive 76, in a similar manner to Embodiment 1. The chassis 2010 and the interior case 2013 are respectively provided with opening 2010c and opening 2013c through which the exhaust pipe 2062 of the holding unit 2006, as described below, is inserted. The holding unit 2003 and the holding unit 2006 are spaced apart from each other in the interior case 2013, and the head 5 can be arranged at a first position facing the holding unit 2003 and at a second position facing the holding unit 2006.

The holding unit 2003 is a first holding unit that includes a workpiece holder 32 and a box-shaped unit body 2031. The unit body 2031 includes a hollow rectangular first section 2311 and a rectangular box-shaped second section 312 that is continuous to the first section 2311 at the +Y direction side-end of the first section 2311. The first section 2311 is secured to a shaft 82 at the −Y direction-side end of the first section 2311. The workpiece holder 32 is secured to the peripheral wall of the second section 312 of the unit body 2031.

The holding unit 2006 is a second holding unit that includes: a tool holder 33 that holds the tool 20; a unit body 2061 that has a rectangular box shape and is filled with refrigerant Re inside; and an exhaust pipe 2062 that is in communication with the inside of the unit body 2061 for discharging the vaporized refrigerant out of the unit body 2061. The unit body 2061 may have a structure that suppresses the transmission of heat from the outside of the unit body 2061 to the refrigerant Re, for example, by forming an air gap (not illustrated) maintained at a relatively high vacuum degree (for example, a vacuum degree of about 10-3 Pa) inside the peripheral wall. The inside of the unit body 2061 is filled with refrigerant Re in such a manner that the refrigerant Re contacts at least a portion of the tool holder 33. For example, liquid nitrogen can be employed as the refrigerant Re. The exhaust pipe 2062 is inserted into the opening 2013c of the interior case 2013 and the opening 2010c of the chassis 2010, and the other end opposite to the end in communication with the inside of the unit body 2061 is disposed outside the chassis 2010. Here, a sealing member (not illustrated) is fitted between the opening 2013c of the interior case 2013 and the exhaust pipe 2062.

Figure 7A:
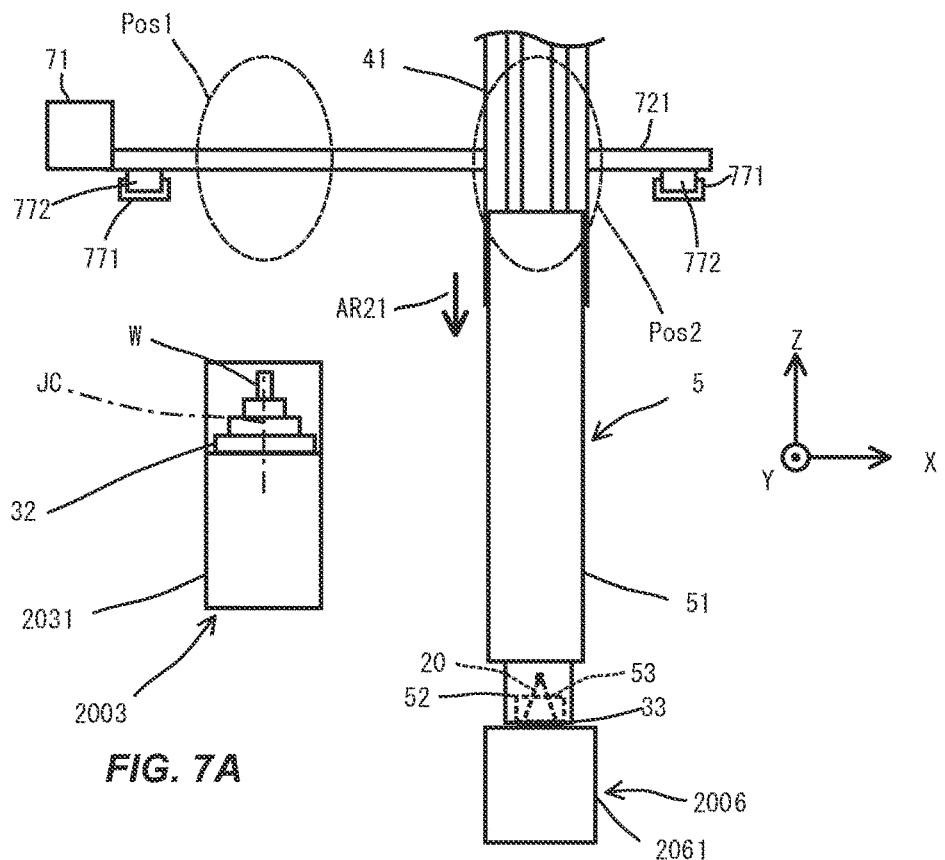
FIG. 7A is a front view illustrating a head of the cutting machining apparatus descending to hold a tool according to Embodiment 2.
Figure 7B:
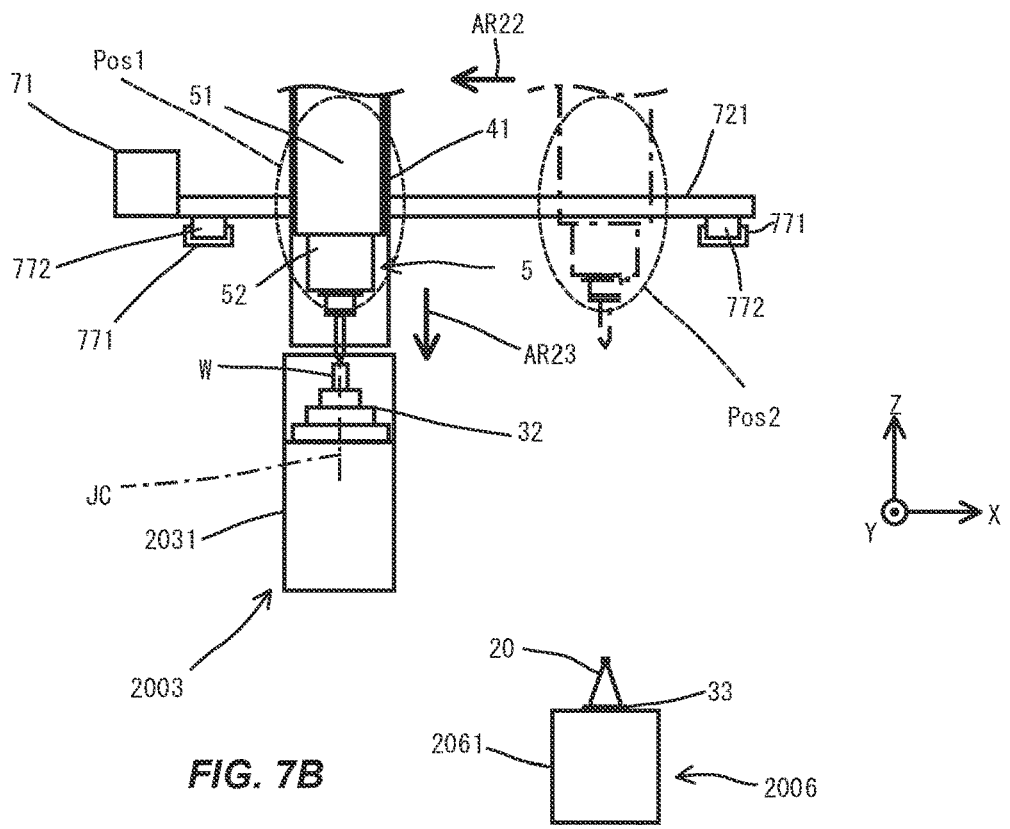
FIG. 7B is a front view illustrating the cutting machining apparatus machining a workpiece according to Embodiment 2.

Next, an operation of the cutting machining apparatus 2001 according to the present embodiment is described with reference to FIGS. 7A and 7B. Here, an example of machining in which the tool 20 is a drill and the tool 20 drills along the longitudinal direction of a long workpiece W is described. It is assumed that tools 20 to be used are held in the three tool holders 33 of the holding unit 2006, and the workpiece W is held in the workpiece holder 32. Furthermore, it is also assumed that the holding unit 2003 is maintained in a posture in which the workpiece holder 32 holding the workpiece W is oriented toward the +Z direction. First, as illustrated in FIG. 7A, in a state in which the head 5 is arranged at a second position Pos2 on the +Z direction side of the tool holder 33 of the holding unit 2006, the cutting machining apparatus 2001 lowers the head 5 in the −Z direction as indicated by the arrow AR 21, causing the head 5 to hold one of the tools 20. The cutting machining apparatus 2001 then raises the head 5 holding the tool 20 in the +Z direction. Subsequently, the cutting machining apparatus 2001 moves the head 5 in the X-axis direction and the Y-axis direction so that the tool 20 is arranged at a first position Pos1 that is in alignment with the workpiece W in the Z-axis direction, as indicated by the arrow AR22. Subsequently, the cutting machining apparatus 2001 performs cutting machining on the workpiece W with the tool 20 by lowering the head 5 in the −Z direction and causing the tip of the tool 20 to contact the workpiece W, as indicated by the arrow AR23, while rotating the rotary spindle 52 without moving the workpiece holder 32.

Note that, when machining is conducted by drilling into the side wall along the longitudinal direction of the workpiece W, the cutting machining apparatus 2001 maintains the workpiece holder 32 in a posture oriented toward the ±X direction by rotating the holding unit 2003 by 90 degrees about the B axis JB. The cutting machining apparatus 2001 then performs cutting machining on the workpiece W with the tool 20 by lowering the head 5 in the −Z direction and causing the tip of the tool 20 to contact the workpiece W, while rotating the rotary spindle 52 without moving the workpiece holder 32. When the tool 20 is a threading tap, the cutting machining apparatus 2001 can also thread the workpiece W at a high speed by lowering the head 5 in the −Z direction and causing the tip of the tool 20 to contact the workpiece W, while rotating the workpiece holder 32 along with rotating the rotary spindle 52.

As described above, with the cutting machining apparatus 2001 according to the present embodiment, the holding unit 2006 holding the tool 20 is separate from the holding unit 2003 holding the workpiece W. As a result, compared to the holding unit 3 according to Embodiment 1, there are fewer constraints on the number of the tool holders 33 provided in the holding unit 2006 or on the arrangement of the tool holders 33. Thus, the holding unit 2006 can hold more tools 20.

Embodiment 3

The cutting machining apparatus according to the present embodiment differs from Embodiment 1 in that a gas inlet hole is provided in the peripheral wall of the unit body of the holding unit for introducing gas present outside the unit body into the inside of the unit body. Meanwhile, the cutting machining apparatus according to the present embodiment includes an airflow generator that generates an airflow that flows from the inside of the interior case into the inside of the unit body through the gas inlet hole, exchanges heat with a tool holder, and then is discharged outside the unit body.

Figure 8:
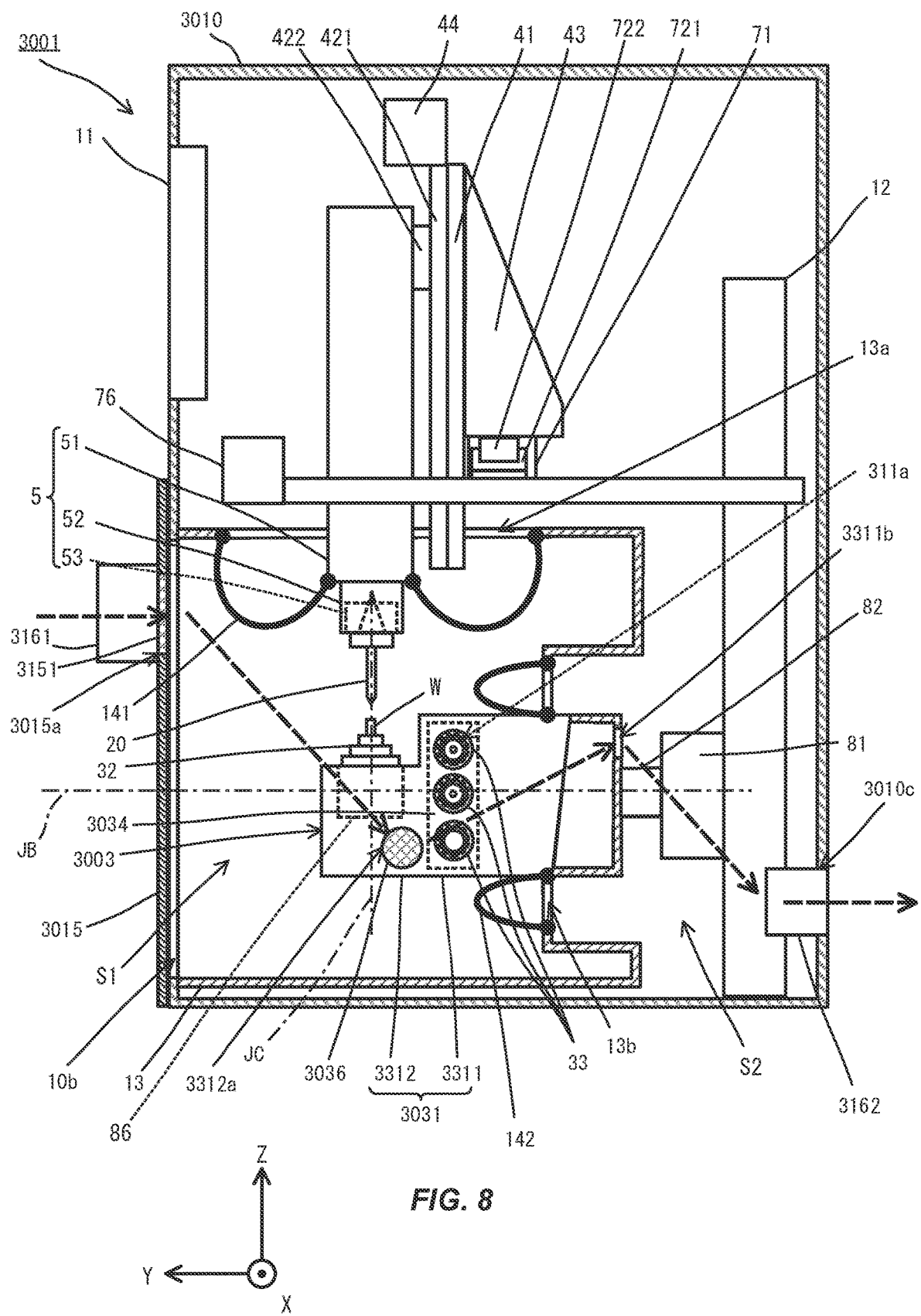
FIG. 8 is a partially broken side view of a cutting machining apparatus according to Embodiment 3 of the present disclosure.

As illustrated in FIG. 8, a cutting machining apparatus 3001 according to the present embodiment includes a head 5, a holding unit 3003 that holds a workpiece W and a tool 20, a controller (not illustrated), a chassis 3010, an interior case 13, a first cover 141, a second cover 142, a door 3015, an intake fan 3161, and an exhaust fan 3162. Note that, in FIG. 8, the same components as those in Embodiment 1 are denoted by the same numeral signs as those in FIG. 2. The cutting machining apparatus 3001 also includes a lift drive 44, an X-direction drive 71, and a Y-direction drive 76, in a similar manner to Embodiment 1. The chassis 3010 has a rectangular box shape and has an opening 3010c formed in a portion of the peripheral wall to which an exhaust fan 3162 is secured. The exhaust fan 3162 is secured to the opening 3010c to discharge gas present in an area S2 outside the interior case 13 within the chassis 3010 out of the chassis 3010. The door 3015 has an opening 3015a formed in part, and a filter member 3151 and an intake fan 3161 are attached to cover the opening 3015a. The intake fan 3161 causes gas present outside the chassis 3010 to flow through the filter member 3151 into the machining area S1 inside the interior case 13. When causing the gas outside the chassis 3010 to flow inside the interior case 13, the filter member 3151 suppresses foreign matters present outside the chassis 3010 from entering the machining area S1 inside the interior case 13. This intake fan 3161 and the aforementioned exhaust fan 3162 function as an airflow generator that generates an airflow that flows from the machining area S1 inside the interior case 13 into the inside of the unit body 3031 and out to the outside of the unit body 3031. Here, the amount of gas inflow by the intake fan 3161 is set to be greater than the amount of gas outflow by the exhaust fan 3162. As a result, the pressure inside the interior case 13 is set to be a positive pressure relative to the pressure outside the interior case 13.

The holding unit 3003 includes a workpiece holder 32, a tool holder 33, a unit body 3031, a heat transfer member 3034, and a filter member 3036. The unit body 3031 includes a hollow rectangular first section 3311 and a rectangular box-shaped second section 3312 that is continuous to the first section 3311 at the +Y direction-side end of the first section 3311. Three openings 311a are formed in the side wall of the first section 3311 along the Z-axis direction. In addition, the unit body 3031 has, in the peripheral wall, a gas inlet hole 3312a for introducing gas present outside the unit body 3031 into the inside of the unit body 3031 and a gas outlet hole 3311b for discharging gas that has been drawn inside the unit body 3031 out of the unit body 3031. Here, the tool holder 33 and the heat transfer member 3034 are disposed between the gas inlet hole 3312a and the gas outlet hole 3311b in the unit body 3031 in the Y-axis direction.

Figure 9:
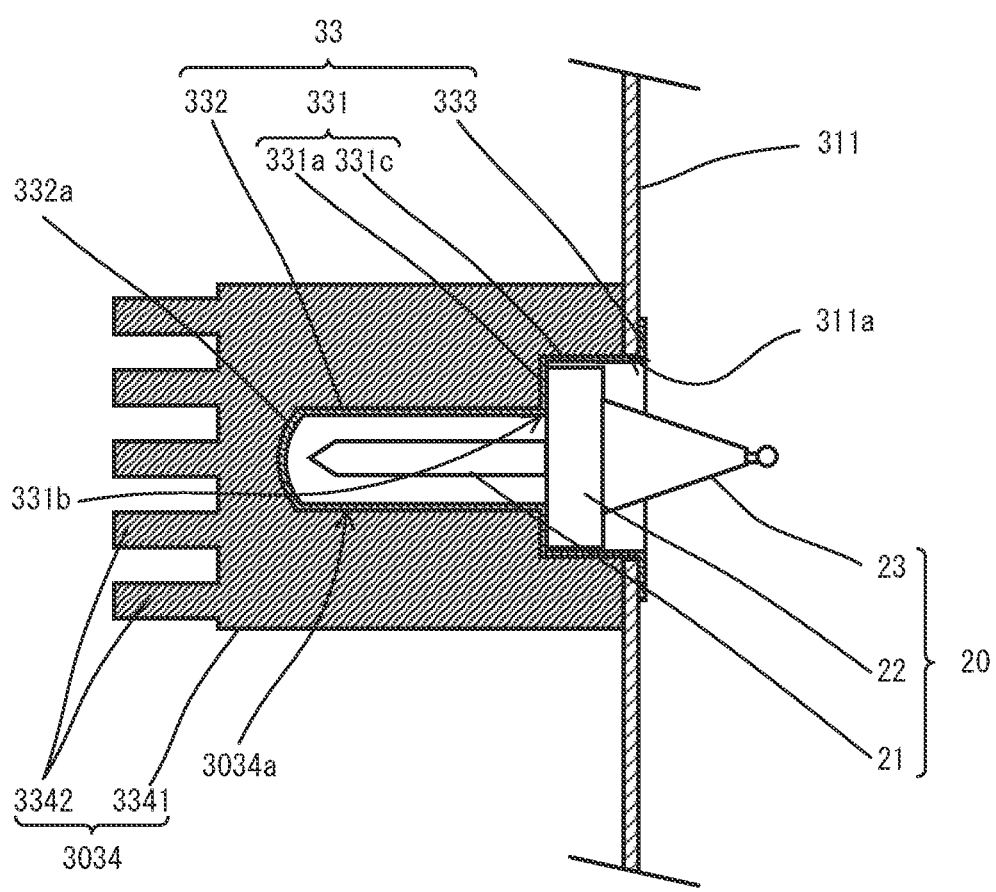
FIG. 9 is a cross-sectional view of a tool holder and a heat transfer member according to Embodiment 3.

The heat transfer member 3034 is formed of metal such as aluminum, copper, and the like, in a rectangular shape and has a rectangular body 3341 and a plurality of heat dissipation fins 3342 protruding from the body 3341, as illustrated in FIG. 9. Note that in FIG. 9, the same components as those in Embodiment 1 are denoted by the same numeral signs as those in FIG. 4A. The body 3341 is arranged to cover the tool body housing 331 and the blade housing 332 of the tool holder 33. In addition, the body 3341 has recesses 3034a that open to portions corresponding to three openings 311a of the unit body 3031 and into which the tool holders 33 are fitted. The tool holder 33 is then fitted inside the recess 3034a of the body 3341 and secured to the body 3341 in a state in which the outer flange 333 is in close contact with the outer periphery of the recess 3034a in the body 3341. Returning to FIG. 8, the filter member 3036 is attached to the unit body 3031 to cover the gas inlet hole 3312a to suppress foreign matters present inside the unit body 3031 from flowing into the machining area S1 inside the interior case 13.

The cutting machining apparatus 3001 according to the present embodiment generates an airflow by driving the exhaust fan 3162, as indicated by the dashed line arrows. Specifically, an airflow occurs that flows from the outside of the chassis 3010 into the machining area S1 inside the interior case 13, thereafter, flows from the gas inlet hole 3312a of the unit body 3031 of the holding unit 3003 into the inside of the unit body 3031, and then flows through the gas outlet hole 3311b of the unit body 3031 out to the area S2 outside the interior case. Here, the gas drawn into the unit body 3031 from the machining area S1 inside the interior case 13 through the gas inlet hole 3312a exchanges heat with the heat transfer member 3034 and then is discharged out of the unit body 3031. As a result, the tool holder 33 and the tool 20 held in the tool holder 33 are cooled via the heat transfer member 3034.

As described above, with the cutting machining apparatus 3001 according to the present embodiment, the tool holder 33 is cooled by an airflow flowing from the machining area S1 inside the interior case 13 to the inside of the unit body 3031 through the gas inlet hole 3312a, exchanging heat with the tool holder 33 and the heat transfer member 3034, and then being discharged to the outside of the unit body 3031. As a result, the tool holder 33 holding the tool 20 can be cooled, thereby suppressing the temperature rise of the workpiece W during machining of the workpiece W.

Embodiment 4

The cutting machining apparatus according to the present embodiment differs from Embodiment 1 in that the present embodiment includes a thermometer that measures the temperature of a tool during machining of a workpiece. When the temperature of the tool measured by the thermometer is greater than or equal to a preset reference temperature, the cutting machining apparatus according to the present embodiment controls the operation of the head to suspend machining of the workpiece and replace the tool.

Figure 10:
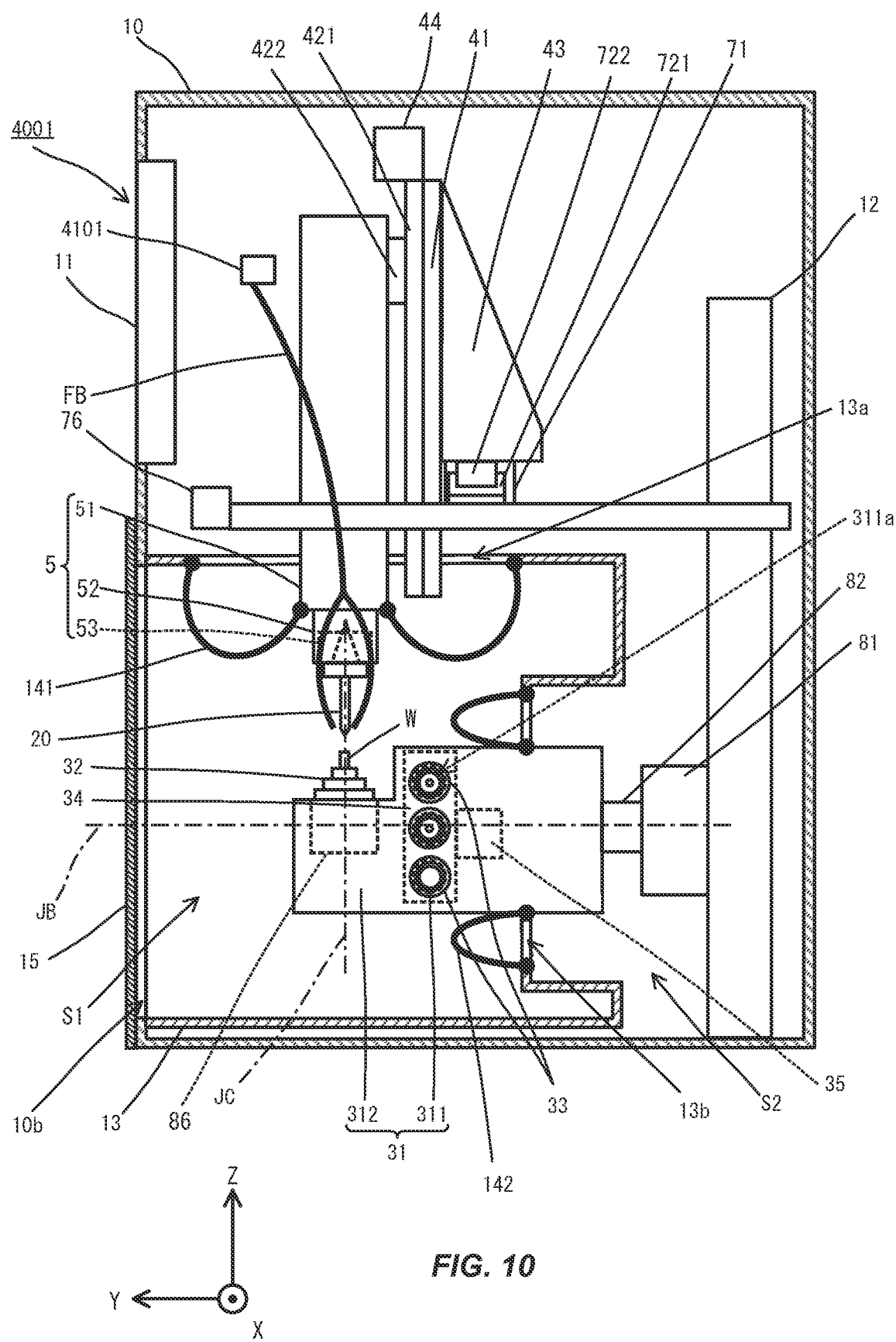
FIG. 10 is a partially broken side view of a cutting machining apparatus according to Embodiment 4 of the present disclosure.

As illustrated in FIG. 10, a cutting machining apparatus 4001 according to the present embodiment includes a head 5, a holding unit 3 that holds a workpiece W and a tool 20, a controller (not illustrated), a chassis 10, an interior case 13, a first cover 141, a second cover 142, a door 15, and a thermometer 4101. Note that, in FIG. 10, the same components as those in Embodiment 1 are denoted by the same numeral signs as those in FIG. 2. The cutting machining apparatus 4001 also includes a lift drive 44, an X-direction drive 71, and a Y-direction drive 76, in a similar manner to Embodiment 1. The thermometer 4101 has an infrared sensor (not illustrated) that is connected to a proximal end of a fiber optic FB of which tips are located near the tool 20 attached to the head 5 and that detects infrared light emitted from the tool 20 and propagating through the fiber optic FB. The thermometer 4101 then calculates the temperature of the tool 20 using the infrared light detected by the infrared sensor based on the preset intensity of the wavelength and outputs temperature information indicating the calculated temperature to the controller.

When the temperature of the tool measured by the thermometer 4101 is greater than or equal to the preset reference temperature, the controller controls the operation of the head 5 to suspend the machining of the workpiece W and replace the tool.

Figure 11:
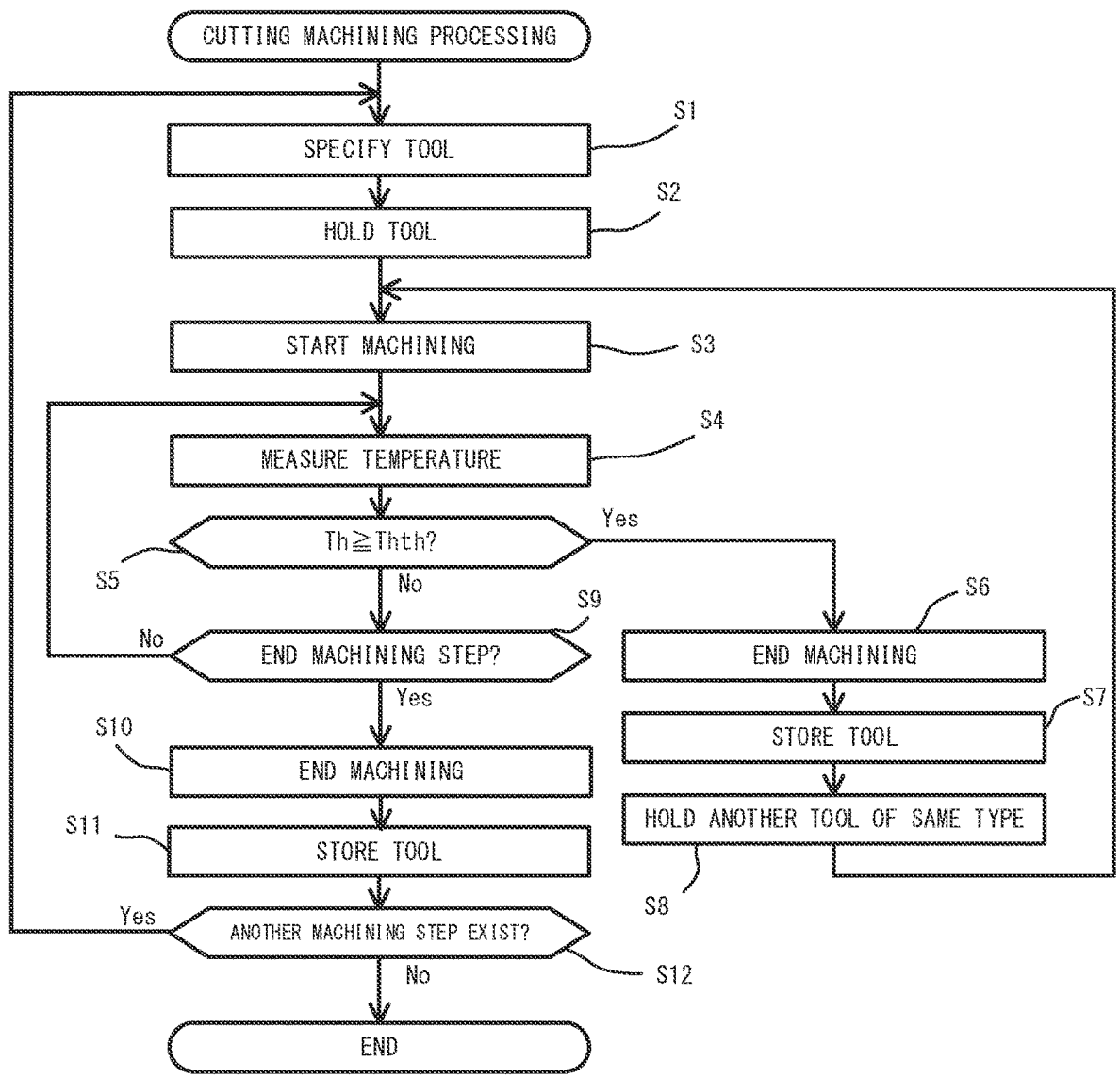
FIG. 11 is a flowchart illustrating an example of a flow of cutting machining processing performed by the cutting machining apparatus according to Embodiment 4.

The following describes an operation of the cutting machining apparatus 4001 according to the present embodiment in detail with reference to FIG. 11. Here, a case where the cutting machining apparatus 4001 performs cutting machining that executes at least one machining step on a workpiece W is described. First, when the cutting machining processing is started, the cutting machining apparatus 4001 specifies a tool to be used at an initial machining step (step S1). Next, the cutting machining apparatus 4001, after setting the holding unit 3 in a posture in which the tool holder 33 is oriented toward the head 5, moves the head 5 in alignment with the +Z direction of the tool holder 33 holding the specified tool 20, and then lowers the head 5 in the −Z direction to cause the head 5 to hold the specified tool 20 (step S2). Then, the cutting machining apparatus 4001 raises the head 5 in the +Z direction and rotates the holding unit 3 about the B axis JB to set the holding unit 32 in a posture in which the workpiece holder 32 holding the workpiece W is oriented toward the +Z direction. The cutting machining apparatus 4001 also moves the head 5 in the X-axis direction so that the position of the tool 20 is in alignment with the workpiece W in the Z-axis direction. Subsequently, the cutting machining apparatus 1 starts cutting machining on the workpiece W by lowering the head 5 in the −Z direction and causing the tool 20 to contact the workpiece W while rotating the rotary spindle 52 or the workpiece holder 32 (step S3).

Thereafter, the cutting machining apparatus 4001 measures the temperature of the tool 20 using the thermometer 4101 (step S4). Next, the cutting machining apparatus 4001 determines whether or not the measured temperature Th of the tool 20 is greater than or equal to the preset reference temperature Thth (step S5). Here, if the cutting machining apparatus 4001 determines that the measured temperature Th of the tool 20 is greater than or equal to the reference temperature Thth (step S5: Yes), the cutting machining apparatus 4001 raises the head 5 in the +Z direction and ends the machining step (step S6). Subsequently, the cutting machining apparatus 4001 stores the tool 20 held by the head 5 in a tool holder 33 by, after setting the holding unit 3 in a posture in which the tool holder 33 is oriented toward the head 5, moving the head 5 to the +Z direction-side of the tool holder 33 that holds no tool 20 and lowering the head 5 in the −Z direction (step S7). The cutting machining apparatus 4001 then raises the head 5 in the +Z direction and moves the head to the +Z direction side of the tool holder 33 that holds another tool 20 of the same type, and then lowers the head 5 in the −Z direction to hold the another tool 20 of the same type (step S8). Next, the cutting machining apparatus 4001 sets the holding unit 3 in a posture in which the workpiece holder 32 holding the workpiece W is oriented toward the +Z direction by raising the head 5 in the +Z direction and then rotating the holding unit 3 about the B axis JB. The cutting machining apparatus 4001 also moves the head 5 in the X-axis direction so that the position of the tool 20 is in alignment with the workpiece W in the Z-axis direction. Subsequently, the cutting machining apparatus 1 starts cutting machining on the workpiece W again by lowering the head 5 in the −Z direction and causing the tool 20 to contact the workpiece W while rotating the rotary spindle 52 or the workpiece holder 32 (step S3).

Whereas, if the cutting machining apparatus 4001 determines in the processing of step S5 that the measured temperature Th of the tool 20 is less than the reference temperature Thth (step S5: No), the cutting machining apparatus 4001 determines whether or not the processing step has ended (step S9). Here, if the cutting machining apparatus 4001 determines that the machining step has not yet ended (step S9: No), the cutting machining apparatus 4001 executes the processing of step S4 again. On the other hand, when the cutting machining apparatus 4001 determines that the machining step has ended (step S9: Yes), the cutting machining apparatus 4001 raises the head 5 in the +Z direction and ends the machining step (step S10). The cutting machining apparatus 4001 then stores the tool 20 held by the head 5 in the tool holder 33 by, after setting the holding unit 3 in a posture in which the tool holder 33 is oriented toward the head 5, moving the head 5 to the +Z direction side of the tool holder 33 that holds no tool 20 and lowering the head 5 in the −Z direction (step S11). Next, the cutting machining apparatus 4001 determines whether or not there is another machining step remaining in the cutting machining processing (step S12). Here, if the cutting machining apparatus 4001 determines that there is another machining step (step S12: Yes), the cutting machining apparatus 4001 specifies a tool to be used in the another machining step (step S1) and executes a series of processing from step S2 onwards. On the other hand, if the cutting machining apparatus 4001 determines that all the machining steps performed in the machining processing have been completed (step S12: No), the cutting machining apparatus 4001 ends the cutting machining processing.

As described above, with the cutting machining apparatus 4001 according to the present embodiment, the temperature of the tool 20 can be maintained below the reference temperature during machining of the workpiece W, thereby suppressing damage to the workpiece W due to an excessive increase in the temperature of the workpiece W during machining of the workpiece W.

Figure 12:
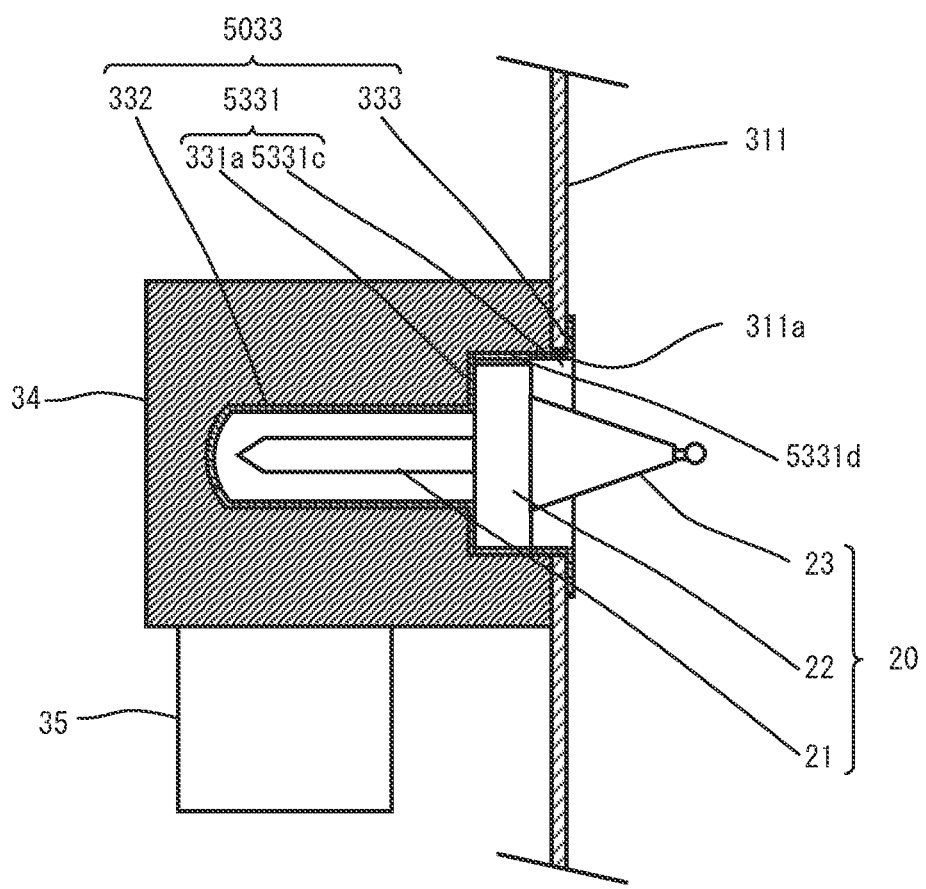
FIG. 12 is a cross-sectional view of a tool holder and a heat transfer member according to a variation.

Although embodiments of the present disclosure have been described above, the present disclosure is not limited to the configurations of the aforementioned embodiments. For example, as illustrated in FIG. 12, the tool body housing 5331 of the tool holder 5033 may be such that only the abutment portion 5311d in the side wall 5331c abutting the tool 20 may be formed of metal. The portion other than the abutment portion 5311d in the tool body housing 5311, that is, the portion other than the abutment portion 5311d in the tool body housing 5331, the blade housing 332, and the outer flange 333, may be formed of resin. Note that, in the tool body housing 5331 of the tool holder 5033, the portion abutting the tool 20 in the bottom wall 331a or both the bottom wall 331a and the side wall 5331c may be formed of metal, and the other portion may be formed of resin.

With such a configuration, the tool holder 5033 can be reduced in weight, and thus the entire cutting machining apparatus can be reduced in weight.

In each embodiment, an example in which the entire tool holder 33 is formed of metal is described without limitation. However, for example, at least one of the tool body housing 331, the blade housing 332, and the outer flange 333 may include a first substrate material formed of resin and a second substrate material formed of a mesh-like braided metal wire embedded within the first substrate material. Here, as the resin forming the first substrate material, for example, polypropylene can be employed. In addition, as the metal wire, for example, an aluminum wire can be employed.

With such a configuration, the tool holder 33 can be reduced in weight, and thus the entire cutting machining apparatus can be reduced in weight.

Although each embodiment describes an example of including three tool holders 33 housing three tools, the number of tool holders 33 is not limited to three, and may be two or fewer, or may be four or more. Although an example in which the tool holders 33 are arranged in a single side wall in the peripheral wall of the unit body 31 has been described, the positions in which the tool holders 33 are arranged in the unit body 31 are not limited thereto. For example, the tool holders 33 may be secured to each of the two opposing sides of the peripheral wall of the unit body 31. In addition, the unit body 31 may be a general bottomed cylindrical shape as a whole, and the tool holder 33 may be disposed along the circumferential direction on the side wall.

Embodiment 3 describes an example in which the holding unit 3003 includes: a heat transfer member 3034 including a rectangular body 3341; and a plurality of heat dissipation fins 3342 protruding from the body 3341. However, the heat transfer member 3034 is not limited thereto and may not have the heat dissipation fins 3342. In addition, although Embodiment 3 describes an example in which the holding unit 3003 includes the heat transfer member 3034, the holding unit 3003 may not be limited thereto and may not have the heat transfer member 3034. In such a case, the holding unit 3003 may have a unit body that has a plurality of openings in the peripheral wall through which tool holders 33 are inserted, and the plurality of tool holders 33 may each be secured to the unit body in a state in which the outer flange 333 is affixed to the outer periphery of each opening in the peripheral wall of the unit body.

The foregoing describes some example embodiments for explanatory purposes. Although the foregoing discussion has presented specific embodiments, persons skilled in the art will recognize that changes may be made in form and detail without departing from the broader spirit and scope of the invention. Accordingly, the specification and drawings are to be regarded in an illustrative rather than a restrictive sense. This detailed description, therefore, is not to be taken in a limiting sense, and the scope of the invention is defined only by the included claims, along with the full range of equivalents to which such claims are entitled.

The present disclosure is suitable as a cutting machining apparatus for cutting machining of bones.

The invention claimed is:
1. A cutting machining apparatus comprising:
a holding unit including:
a workpiece holder holding a workpiece;

a tool holder of a bottomed cylindrical shape holding a tool in a state in which the tool is inserted inside; and a unit body securing the tool holder in such a way that, in a state in which the tool is not inserted in the tool holder, an inside of the tool holder is in communication with an outside and an outer wall of the tool holder is isolated from the outside;

a head including a chuck positioned facing the holding unit and the chuck holding the tool held by the tool holder;

an interior case including, in a peripheral wall, a first opening through which the holding unit is inserted and a second opening through which the head is inserted, the interior case housing the workpiece holder, the tool holder, and the chuck disposed inside;

a first cover formed of a soft material and occluding between the holding unit and an outer periphery of the first opening in the interior case;

a second cover formed of a soft material and occluding between the head and an outer periphery of the second opening in the interior case; and a cooling mechanism cooling the tool holder from within the unit body.

2. The cutting machining apparatus according to claim 1, wherein the tool includes:

a tool body of a plate shape;

a blade for cutting the workpiece, the blade being formed continuously with the tool body and protruding from one surface side in a thickness direction of the tool body; and a shank formed continuously with the tool body and protruding from the other surface side in the thickness direction of the tool body, the shank being held by the chuck, and the tool holder holds the tool in a state in which the shank is exposed outside the holding unit within the interior case.

3. The cutting machining apparatus according to claim 2, wherein the tool holder includes:

a tool body housing of a bottomed cylindrical shape including a through hole formed in a first bottom wall penetrating in a thickness direction of the first bottom wall, the tool body being disposed inside the tool body housing in a state in which the tool body abuts at least one of the first bottom wall and a side wall;

a blade housing of a bottomed cylindrical shape in which an entire end portion opposite a second bottom wall side is formed continuously with an outer periphery of the through hole in the first bottom wall, the blade being disposed inside the blade housing; and an outer flange extending from an end opposite the first bottom wall side of the tool body housing in a direction orthogonal to a cylindrical axis of the tool body housing, as well as, away from the cylindrical axis of the tool body housing, the cooling mechanism includes a heat transfer member arranged to cover at least one of the tool body housing and the blade housing, and the outer flange is secured to an exposed portion of the heat transfer member outside the unit body.

4. The cutting machining apparatus according to claim 3, wherein the tool body housing portion includes a portion formed of metal in the first bottom wall or side wall abutting the tool and the other portion formed of resin.

5. The cutting machining apparatus according to claim 3, wherein at least one of the tool body housing, the blade housing, and the outer flange includes:

a first substrate material formed of resin; and a second substrate material formed of a mesh-like braided metal wire and embedded within the first substrate material.

6. A cutting machining apparatus, comprising:

a first holding unit including a workpiece holder that holds a workpiece;

a second holding unit including:

a tool holder of a bottomed cylindrical shape holding a tool in a state in which the tool is inserted inside; and a unit body securing the tool holder in a state in which an outer wall of the tool holder is isolated from the outside, in which an inside of the tool holder is in communication with an outside in a state in which the tool is not inserted in the tool holder;

a head including a chuck that can be arranged at a first position facing the first holding unit and at a second position facing the second holding unit and holds the tool held by the tool holder;

an interior case including, in a peripheral wall, a second opening through which the head is inserted and housing at least the workpiece holder, the tool holder, and the chuck disposed inside; and a cover formed of a soft material and occluding between the head and an outer periphery of the second opening in the interior case, wherein refrigerant is filled inside the unit body in a manner that the refrigerant contacts at least a portion of the tool holder.

7. A cutting machining apparatus, comprising:

a holding unit including:

a workpiece holder holding a workpiece;

a tool holder of a bottomed cylindrical shape holding a tool inside in a state in which the tool is inserted inside; and a unit body securing the tool holder in a state in which an outer wall of the tool holder is isolated from the outside, in which an inside of the tool holder is in communication with an outside in a state in which the tool is not inserted in the tool holder, and the unit body is provided with a gas inlet hole in a peripheral wall for introducing an external gas present outside;

a head including a chuck positioned facing the holding unit and the chuck holding the tool held by the tool holder;

an interior case including, in a peripheral wall, a first opening through which the holding unit is inserted and a second opening through which the head is inserted, the interior case housing the workpiece holder, the tool holder, and the chuck disposed inside;

a first cover formed of a soft material and occluding between the holding unit and an outer periphery of the first opening in the interior case;

a second cover formed of a soft material and occluding between the head and an outer periphery of the second opening in the interior case; and an airflow generator generating an airflow that flows from an inside of the interior case to an inside of the unit body through the gas inlet hole, exchanges heat with the tool holder, and then is discharged outside the unit body.

8. The cutting machining apparatus according to claim 7, wherein the airflow generator comprises:

an intake fan that causes gas present outside the interior case to flow inside the interior case; and an exhaust fan that causes gas present inside the interior case to flow inside the unit body through the gas inlet hole and to be discharged outside the unit body, a pressure inside the interior case is set to be a positive pressure relative to a pressure outside the interior case by setting an amount of gas inflow by the intake fan to be greater than an amount of gas outflow by the exhaust fan.

9. The cutting machining apparatus according to claim 7, wherein the unit body further comprises a gas outlet hole for discharging, outside of the unit body, gas that has been drawn inside the unit body, and the tool holder is disposed between the gas inlet hole and the gas outlet hole of the unit body.

10. The cutting machining apparatus according to claim 1, further comprising:

a thermometer measuring a temperature of the tool during machining of the workpiece; and a controller, when the temperature of the tool is greater than or equal to a preset reference temperature, controlling an operation of the head to suspend machining of the workpiece and replace the tool.

11. The cutting machining apparatus according to claim 8, wherein the unit body further comprises a gas outlet hole for discharging, outside of the unit body, gas that has been drawn inside the unit body, and the tool holder is disposed between the gas inlet hole and the gas outlet hole of the unit body.

12. The cutting machining apparatus according to claim 2, further comprising:

a thermometer measuring a temperature of the tool during machining of the workpiece; and a controller, when the temperature of the tool is greater than or equal to a preset reference temperature, controlling an operation of the head to suspend machining of the workpiece and replace the tool.

13. The cutting machining apparatus according to claim 3, further comprising:

a thermometer measuring a temperature of the tool during machining of the workpiece; and a controller, when the temperature of the tool is greater than or equal to a preset reference temperature, controlling an operation of the head to suspend machining of the workpiece and replace the tool.

14. The cutting machining apparatus according to claim 4, further comprising:

a thermometer measuring a temperature of the tool during machining of the workpiece; and a controller, when the temperature of the tool is greater than or equal to a preset reference temperature, controlling an operation of the head to suspend machining of the workpiece and replace the tool.

15. The cutting machining apparatus according to claim 5, further comprising:

a thermometer measuring a temperature of the tool during machining of the workpiece; and a controller, when the temperature of the tool is greater than or equal to a preset reference temperature, controlling an operation of the head to suspend machining of the workpiece and replace the tool.

16. The cutting machining apparatus according to claim 6, further comprising:

a thermometer measuring a temperature of the tool during machining of the workpiece; and a controller, when the temperature of the tool is greater than or equal to a preset reference temperature, controlling an operation of the head to suspend machining of the workpiece and replace the tool.

17. The cutting machining apparatus according to claim 7, further comprising:

a thermometer measuring a temperature of the tool during machining of the workpiece; and a controller, when the temperature of the tool is greater than or equal to a preset reference temperature, controlling an operation of the head to suspend machining of the workpiece and replace the tool.

18. The cutting machining apparatus according to claim 8, further comprising:

a thermometer measuring a temperature of the tool during machining of the workpiece; and a controller, when the temperature of the tool is greater than or equal to a preset reference temperature, controlling an operation of the head to suspend machining of the workpiece and replace the tool.

19. The cutting machining apparatus according to claim 9, further comprising:

a thermometer measuring a temperature of the tool during machining of the workpiece; and a controller, when the temperature of the tool is greater than or equal to a preset reference temperature, controlling an operation of the head to suspend machining of the workpiece and replace the tool.

20. The cutting machining apparatus according to claim 11, further comprising:

a thermometer measuring a temperature of the tool during machining of the workpiece; and a controller, when the temperature of the tool is greater than or equal to a preset reference temperature, controlling an operation of the head to suspend machining of the workpiece and replace the tool.

* * * * *

UNITED STATES PATENT AND TRADEMARK OFFICE
CERTIFICATE OF CORRECTION

| | | |
|---|---|---|
| PATENT NO. | : 12,390,228 B2 | Page 1 of 1 |
| APPLICATION NO. | : 18/335389 | |
| DATED | : August 19, 2025 | |
| INVENTOR(S) | : Tsuji et al. | |

It is certified that error appears in the above-identified patent and that said Letters Patent is hereby corrected as shown below:

On the Title Page

Item (73)
Please change "Nissin Manufacturing Co., Ltd." to --Nissin Fulfil CO., Ltd.--

Signed and Sealed this
Second Day of December, 2025

John A. Squires
*Director of the United States Patent and Trademark Office*